(12) United States Patent
Lu et al.

(10) Patent No.: US 7,575,628 B2
(45) Date of Patent: *Aug. 18, 2009

(54) HYDRAULIC CEMENT COMPOSITIONS AND METHODS OF MAKING AND USING THE SAME

(75) Inventors: Donghui Lu, Vancouver (CA); Shuxin Zhou, Vancouver (CA)

(73) Assignee: Innovative BioCeramix, Inc., Vancouver, B.C. (CA)

( * ) Notice: Subject to any disclaimer, the term of this patent is extended or adjusted under 35 U.S.C. 154(b) by 218 days.

This patent is subject to a terminal disclaimer.

(21) Appl. No.: 11/390,702

(22) Filed: Mar. 27, 2006

(65) Prior Publication Data

US 2006/0213395 A1 Sep. 28, 2006

Related U.S. Application Data

(60) Provisional application No. 60/664,977, filed on Mar. 25, 2005.

(51) Int. Cl.
 *A61L 24/02* (2006.01)
 *C04B 7/02* (2006.01)
 *C04B 12/02* (2006.01)

(52) U.S. Cl. .................. 106/640; 106/35; 106/717; 106/735; 106/737; 623/23.62; 424/602

(58) Field of Classification Search ............ 106/640, 106/717, 35, 735, 737
See application file for complete search history.

(56) References Cited

U.S. PATENT DOCUMENTS 3,409,452 A * 11/1968 Angstadt et al. ............ 106/717
3,510,322 A * 5/1970 Kuneo et al. ................ 106/35
5,415,547 A   5/1995 Torabinejad et al.
5,769,638 A   6/1998 Torabinejad et al.
6,518,212 B1 * 2/2003 Wagh et al. ................. 501/111

(Continued)

FOREIGN PATENT DOCUMENTS

WO    WO02056838    7/2002

OTHER PUBLICATIONS

Steinke et al., Development of chemically bonded ceramincs in the CaO—SiO2—P2O5—H2O system. Materials Research Laboratory. Online Feb. 12, 2003 abstract only.

(Continued)

*Primary Examiner*—C. Melissa Koslow
(74) *Attorney, Agent, or Firm*—Todd N. Hathaway (57) ABSTRACT

A hydraulic cement comprising a calcium silicate and at least one phosphate compound. The phosphate compound is included in an amount sufficient to react a major portion of the calcium hydroxide that is produced during hydration of the cement to hydroxyapatite or other calcium phosphates. The phosphate compound is preferably a mono-calcium phosphate. The cement is useful in both bio-medical/dental and engineering applications. The calcium hydroxide is reacted by the phosphate to form hydroxiapatite or other calcium phosphate that is co-precipitated with the calcium silicate hydrate to form a composite-like structure on a nano-scale level. The reduced calcium hydroxide content in the set cement increases its strength and reduces its pH. The hydroxiapatite content and the reduced pH render the cement bioactive and suitable for use in medical and dental implants, for example, for replacement bone and tooth material. Due to its high strength, the cement may also be used for structural/engineering applications.

16 Claims, 6 Drawing Sheets

U.S. PATENT DOCUMENTS

| | | |
|---|---|---|
| 6,730,324 B2 | 5/2004 | Troczynski et al. |
| 7,083,672 B2 * | 8/2006 | Wagh et al. .................... 106/35 |
| 2003/0159618 A1 | 8/2003 | Primus |
| 2006/0078590 A1 * | 4/2006 | Hermansson et al. ....... 424/426 |

OTHER PUBLICATIONS

Vaidya et al., Pressure-induced crystalline to amorphous transition in hydroxylapatite. J. of Materials Science 32, 3213-3217 (1997).

Persson, Bertil, Seven-year study on the effect of silica fume in concrete. Elsevier Science Ltd., 1998.

Mitchell et al., Osteoblast biocompatibility of mineral trioxide aggregate, Biomaterials 20, 167-173 (1999).

Hamanishi et al., Self-setting, bioactive, and biodegradable TTCP-DCPD apatite cement. J. of Biomedical Materials Research, 32, 383-389 (1996).

Diarra et al., Elaboration and evaluation of an intraoral controlled release delivering system. Biomaterials, 19, 1523-1527 (1998).

Oonishi et al., Particulate bioglass compared with hydroxyapatite as a bone graft substitute (Research) 1996.

* cited by examiner

HYDRAULIC CEMENT COMPOSITIONS AND METHODS OF MAKING AND USING THE SAME

RELATED APPLICATIONS

This application claims the benefit of U.S. Provisional Patent Application No. 60/664,977 filed on 25 Mar. 2005.

BACKGROUND

1. Field of the Invention

The present invention relates to high-strength hydraulic cement compositions, and, more particularly, to high-strength hydraulic cement compositions comprising phosphate compounds and calcium silicates, and methods for making and using the same.

2. Related Art

Hydraulic cements have very long history, but many aspects of their chemistry have yet to be completely understood.

Thousands of years ago, Pozzolana, a volcanic ash from Mount Vesuvius, was mixed with limestone, to prepare a powder that hardened ("set") when mixed water. This pozzolanic (natural) cement was later reproduced artificially, by heat treating of a mixture of limestone, clay, and bauxite at temperatures in excess of 1500 C. The resulting cement "clinker" was crushed and mixed with gypsum and other additives to result in ordinary Portland cement (OPC). The process is largely unchanged today, although minor changes in composition and various additives have been introduced to achieve particular properties. Current global production of OPC approaches 1 T for every person on earth each year, consuming vast amounts of resources and energy; thus any modification which would decrease the use of resources, while maintaining or improving the properties of cement, could have a significant impact on the environment and our civilization.

There are two main compounds in Portland cement: dicalcium silicate (C2S, also known as Alite) and tricalcium silicate (C3S, also known as Belite). Highly crystalline calcium hydroxide ($Ca(OH)_2$) (referred to herein as CH) and amorphous calcium-silicate-hydrate (referred to herein as C—S—H) are formed in the hydration of these two principal components (C2S and C3S). The hydrated cement paste consists of approximately 70% C—S—H, 20% $Ca(OH)_2$, 7% sulfoaluminate, and 3% secondary phases. Major problems caused by the calcium hydroxide, which is formed as a result of the setting reaction, are that CH is soluble in water and has low strength, which properties negatively affect the quality of concrete; as will be discussed below, the present invention decreases the final content of CH in the set cement, thus resulting in a significantly increased durability and strength.

General purpose Portland type cement (ASTM I) typically contains approximately 50% C3S, 25% C2S, 12% C3A (tricalcium aluminate $3CaO.Al_2O_3$), 8% C4 AF (tetracalcium aluminoferrite $4CaO.Al_2O_3.Fe_2O_3$), and 5% calcium oxide CaO. The total amount of calcium silicates (C3S and C2S) is approximately 75%, with the predominant silicate being C3S.

A number of investigators have reported achieving an improvement in the mechanical strength of Portland cement, by adding silica fume ($SiO_2$, referred to as S) in order to decrease calcium hydroxide content in the hydrated cement (Mitchell, et al, "Interaction of silica fume with calcium hydroxide solutions and hydrated cement pastes", *Cement and Concrete Research* (1998), 28(11), 1571-1584 and Persson "Seven-year study on the effect of silica fume in concrete" *Advanced Cement Based Materials* (1998), 7(3/4), 139-155). The mechanism of improvement depends on the silica fume reacting with calcium hydroxide to produce an amorphous C—S—H gel with a high density and low Ca/Si ratio. Therefore, no new phases are introduced to the set cement. This demonstrates that removal of CH from the set cement provides a substantial improvement in quality. The present invention discloses an alternative method of in-situ removal of CH from setting cement, by reactively precipitating calcium phosphates, in particular hydroxyapatite; this provides not only enhanced strength and degradation resistance but also enhanced biological properties.

Phosphate-based hydraulic structural cements ares well known (e.g., see Friedman et al "BoneSource hydroxyapatite cement: a novel biomaterial for craniofacial skeletal tissue engineering and reconstruction" *Journal of Biomedical Materials Research* (1998), 43(4), 428-432). However, these cements do not contain silicate material. Strength development and hardening of these cements during setting does not rely on hydration of calcium silicates, and does not involve precipitation of C—S—H gel and CH.

Ma et al ("Effect of phosphate additions on the hydration of Portland cement" *Advances in Cement Research* (1994), 6(21), 1-12) reported the effect of phosphate additions on the hydration process of Portland cement. The reaction products were amorphous, but hydrothermal treatment at 160° C. of ordinary Portland cement (OPC) modified by $CaHPO_4$ allowed transformation of a poorly crystalline phosphate phase into hydroxyapatite. Generally, the presence of sodium and calcium phosphates resulted in improved flexural strengths. However, a number of disadvantages limit the usefulness of the process disclosed by Ma et al, such as the need for hydrothermal treatment to form hydroxyapatite and the need for high pressure (28 MPa) pressing in order to prepare samples having adequate strength. Also, the process described by Ma et al cannot be used to form a uniform composite structure, and the mechanical strength of the phosphate-modified samples was not significantly improved by comparison with Ordinary Portland cement Chemically bonded ceramics (CBC), in the system CaO—$SiO_2$—$P_2O_5$—$H_2O$, were investigated by Hu et al ("Investigation of hydration phases in the system CaO—$SiO_2$—$P_2O_5$—$H_2O$" *J. Mater. Res.* 1988, 3(4) 772-78) and Sterinke et al (Development of chemically bonded ceramics in the system CaO—$SiO_2$—$P_2O_5$—$H_2O$" *Cement and Concrete Res.* 1991 (21)66-72). CBC powders were synthesized by a sol-gel process and then fired at a temperature of 700-1000 C for 2 hours. The components of the powders before hydration are calcium hydroxyapatite (major), calcium silicate hydrate, γ-$2CaO.SiO_2$, amorphous calcium silicate, and amorphous calcium phosphate (Hu, et al, "Studies of strength mechanism in newly developed chemically bonded ceramics in the system CaO—$SiO_2$—$P_2O_5$—$H_2O$" *Cement and Concrete Res.* 1988 (18)103-108). However, the mechanical properties were not improved when the samples were hydrated at room temperature. Also, since the hydroxyapatite phase precipitated before hydration of the cement (i.e., it did not participate in the cement hydration), it did not reinforce the cement and thus did not contribute to its increased strength. In order to increase the mechanical strength of CBC, the samples were formed under high pressure (345 MPa) and were hydrated at high temperature.

Recently, Portland cement based materials (referred to as mineral trioxide aggregate, MTA) have been used for dental applications, such as endodontic dental treatment (Vargas et al., "A Comparison of the In vitro Retentive Strength of Glass-Ionomer Cement, Zinc-Phosphate Cement, and Mineral Trioxide Aggregate for the Retention of Prefabricated Posts in Bovine Incisors" *J. Endodont.* 30(11) 2004, 775-777). MTA consists primarily of tricalcium silicate, tricalcium oxide and silicate oxide. (Torabinejad et al. "Physical and chemical properties of a new root-end filling material". *J. Endodont* 21(1995) 349-253). It is used in many surgical and nonsurgical applications, and possesses the biocompatibility and sealing abilities requisite for a perforation material (Lee, et al, "Sealing ability of a mineral trioxide aggregate for repair of lateral root perforations" *J Endod* 1993; 19:541-4.). It can be used both as a nonabsorbable barrier and restorative material for repairing root perforations. Because it is hydrophilic and requires moisture to set, MTA is the barrier of choice when there is potential for moisture contamination, or when there are restrictions in technical access and visibility.

The physical and chemical properties of MTA have been tested and the initial pH on mixing was 10.2 rising to 12.5 after 3 hours. The MTA was demonstrated to be significantly less toxic than other root-end filing materials when freshly mixed, and toxicity was negligible when fully set at 24 h (Mitchell, et al, "Osteoblast biocompatibility of mineral trioxide aggregate" *Biomaterials* 20 (1999) 167-173) it also has good compressive strength after setting.

Torabinejad et al (U.S. Pat. No. 5,415,547 and U.S. Pat. No. 5,769,638) disclosed an improved method for filling and sealing tooth cavities using an MTA cement composition. The cement composition resembles Portland cement, and formed an effective seal against re-entrance of infectious organisms. However, the cement was gray in color, which is unsuitable for most dental applications. Moreover, although the MTA cement has been demonstrated to be non-toxic towards living tissue, it contains aluminum which is not well accepted by living tissue if released in ionic form. The hydration product of calcium aluminates are a mixture of calcium-sulfate-aluminate compounds (*Concerte*, J. F. Young, pp 76-98, Prentice-Hall, Inc, Englewood Cliffs, 1981). In permanent and long term implants, such as dental fillings, bone implants, and orthopedic surgery, the calcium sulfate aluminates will continually release aluminum ions into the human biological system (Fridland, et al., "MTA Solubility: A Long Term Study", JOE—Volume 31, Number 5, May 2005, and *Journal of Endodontics*, Vol. 29, No. 12, December 2003). Considerable literature indicates that aluminum ions are toxic to human biological systems. For example, aluminum directly inhibits mineralization of bone or is toxic to the osteoblast. Diseases that have been associated with aluminum include dialysis dementia, renal osteodystrophy and Alzheimer's disease; aluminum also has an effect on red blood cells, parathyroid glands and chromosomes.

Recently, a white form of MTA (which is substantially iron-free) has been released, which addressed the concerns related to color-compatibility for dental applications. However, the modified "white" MTA is still essentially OPC with aluminum as one of its components. Primus (US Pat. Appl. No. 20030159618) disclosed a process for making a white, substantially non-iron containing dental material formed from Portland cement. The material still contains aluminum in its chemical composition. Moreover, while this process decreases the iron content it does not improve the biological properties of these materials, because it does not include any calcium phosphate phases and in particular does not include hydroxyapatite.

Hydraulic calcium phosphate cements (CPC) are another material widely used for variety of bio-medical applications. CPC was first reported in a binary system containing tetracalcium phosphate (TTCP) and dicalcium phosphate anhydrate (DCPA) (L. C. Chow et al. *J. Dent Res.*, 63, 200, 1984). The CPC advantages include self-setting (similar to OPC), but additionally it includes an apatitic phase in the set cement (e.g. HAP) Consequently, CPC is a bio-active material actively interacting with body fluids through dissolution-re-precipitation process. This has led to applications such as bone replacement and reconstruction, and also drug delivery devices (M. Dairra, et al. *Biomaterials,* 19 1523-1527, 1998; M. Otsuka, et al. *J. of Controlled Release* 43(1997)115-122, 1997; Y. Tabata, *PSTT*, Vol. 3, No. 3, 80-89, 2000; M. Otsuka, et al. *J. of Pharm. Sci.* Vol. 83, No. 5, 1994). Research into CPC is quite active, and two inventors in the present matter were also co-inventors in U.S. Pat. No. 6,730,324 which disclosed a novel process for CPC and its applications.

CPC is typically formulated as a mixture of solid and liquid components in pertinent proportions, which react to form the apatite HAP. The physicochemical reactions that occur upon mixing of the solid and liquid components are complex, but dissolution and precipitation are the mechanisms primarily responsible for the final apatite formation (C. Hamanish et al J. Biomed. Mat. Res., Vol. 32, 383-389, 1996; E. Ferandez et al J. Mater. Sci. Med. 10, 223-230, 1999). The reaction pathway in most CPC systems does not lead to stoichiometric HAP, but rather to calcium-deficient $Ca_{10-x}(HPO_4)_x(PO_4)_{6-x}(OH)_{2-x}$, similar to that found in bone. The major drawback of CPC technology is low mechanical strength (generally below 20 MPa compressive), which extremely limits its applications for medical materials and devices.

Silica also enhances the bioactive properties of materials. A combination of the oxides of calcium, phosphorous and silicon in proper proportions (with a majority of silica, of about 45 wt %) results in a well known bioactive glass material, with excellent in-vivo performance and stimulation of cell growth (e.g. Oonishi et al, "Particulate Bioglass compared with hydroxyapatite as a bone graft substitute", *J. Clin. Orthop. Rel. Res.* 334, 316-25, 1997; also U.S. Pat. No. 5,811, 302 by Ducheyne et al, Sep. 22, 1988). Unfortunately, although chemically advantageous, bio-glass must be processed at very high temperatures (generally in excess of 1000 C), and is rather a dense, weak and brittle material. Another disadvantage of bio-glass is that it does not easily dissolve in biological environment (due to dense $SiO_2$ film coverage), which is desirable in some applications, e.g., for stimulation of bone growth.

The literature has reported recent attempts to address these issues, by combining the three oxides of calcium, phosphorous and silicon into porous crystalline composite material, which would possess high bioactivity similar to the bio-glass, but which would be stronger (even though porous) and easier to resorb in-vivo (A. R. El-Ghannam, "Advanced bioceramics composite for bone tissue engineering: design principles and structure-bioactivity relationship", *J. Biomed. Mater. Res.* 69A, 490-501, 2004). The precursors to the three oxides (plus sodium oxide) were heat treated at high temperatures (130-800 C) to result in a porous composite of crystalline silica and variety of calcium-phosphates or calcium-sodium-phosphates. Excellent bioactivity of these composites was demonstrated. Unfortunately the need for the high temperature treatment makes this composite material difficult to use as biomaterial, as all the processing and shaping operations must take place outside of the application/implantation site.

Accordingly, there exists a need for a hydraulic cement having improved properties, in particular high early strengths, high overall compressive strength, rapid setting time, low hydration heat, resistance to degradation, and good expansiveness to offset shrinkage. Still further, there exists a need for such a hydraulic cement that can be readily modified to have biocompatible and bioactive properties, so as to be useful for medical and dental applications, as well as engineering applications.

SUMMARY OF INVENTION

The present invention discloses new high strength bioactive hydraulic cement calcium phosphate silicate cement (CPSC) compositions and methods of making them and using them in variety of engineering and non-engineering applications. Due to the unique combination of properties of CPSC, examples include uses in such widely diversified fields as construction and medical/dental materials and devices. It will be understood that those skilled in the relevant arts may identify numerous other uses for the cement of the present invention, even if not specifically indicated in the present disclosure.

The CPSC cements of the present invention have relatively high mechanical strength (e.g. in comparison to OPC or CPC), relatively high-stability against corrosive environments, and adjustable setting and hardening times. In contrast to previously compositions, the CPSC provided by the present invention is self-setting at room temperature and pressure, with higher early strength and low hydration heat. In addition to the above properties, which are valuable in structural applications of CPSC, the cements contain significant amounts of calcium phosphate (particularly hydroxyapatite) and are therefore highly bioactive, highly biocompatible, and extremely durable in variety of biological environments.

The hydraulic cement compositions comprise at least one phosphate compound and at least one calcium silicate compound. Variants include compositions similar to Ordinary Portland Cement (OPC), modified through addition of phosphate compounds. Other variants are calcium-silicate containing cements unlike OPC compositions.

In a preferred embodiment, the main components of the CPSC cement are (i) calcium oxide (CaO) in the range of about 45%-80% by weight of the cement composition, preferably 55 wt %-70 wt %, (ii) silica ($SiO_2$) in range of 10%-35% by weight preferably 15 wt %-30 wt %, and (iii) phosphate (in the form of $P_2O_5$ or alternative ionic form) in range of 1%-30% by weight preferably 3 wt %-15 wt %.

Complex chemical and physical reactions and processes take place after the hydraulic CPSC cement powder components are mixed with water. These reactions involve hydration of calcium silicate compounds and the dissolution of phosphate compounds, and co-precipitation of calcium phosphates, such as hydroxyapatite and calcium silicate hydrate gel. A key discovery is that the dissolution of phosphate compounds and precipitation of calcium phosphates takes place during, and utilizes the by-products of, the hydration of calcium silicate compounds, such as calcium hydroxide, to further precipitate additional calcium phosphate compounds. Additionally, the co-precipitating calcium silicate hydrate gel consumes water available from the decomposition of phosphate precursors to the hydroxyapatite. It is therefore believed that the setting process of CPSC is a new and complex phenomenon discovered for the Ca—P—Si—O—H system.

Another aspect of the present invention is directed to high strength cement compositions obtained through modification of Ordinary Portland cement (OPC) by addition of phosphate ions. The inorganic chemical phosphate modifier, preferably monocalcium phosphate. reacts in-situ with the calcium hydroxide (CH) that forms during hydration of the PC components (i.e. mainly di-calcium silicate C2S and tri-calcium silicate C3S), thus removing the CH which is the structurally weak component in the body of set cement. Reaction of CH with the phosphates leads to precipitation of calcium phosphates, in particular hydroxyapatite (HAP). Such Calcium Phosphate Silicate Cement (CPSC) has enhanced functionality, in particular enhanced corrosion resistance (due to absence of CH) and enhanced biocompatibility and bioactivity (due to the presence of HAP).

Therefore, in one embodiment OPC is modified to produce CPSC. During setting of such cement the phosphate ions react with the excess calcium hydroxide (CH) resulting from the hydration of the principal components of OPC, i.e., di-calcium silicate ($2CaO.SiO_2$ or C2S) and tri-calcium silicates ($3CaO.SiO_2$ or C3S). Ordinarily, in the absence of the phosphate ions, the CH forms inclusions of variable size and shape in the principal gel ($CaO—SiO_2—H_2O$ gel, also expressed as C—S—H) structure of the set PC. These CH inclusions are weak spots structurally and chemically, i.e. they do not contribute strength but rather weaken OPC, and additionally are sensitive to environmental effects (up to 25 wt % of such CH may accumulate within the body of unmodified OPC).

The present invention reacts phosphate ions with the CH that is produced during OPC hydration, to form variety of calcium phosphate inclusions, the most stable and strongest being hydroxyapatite (HAP). The HAP inclusions in CPSC contribute substantially to the overall compressive strength of the set cement, both directly (through bonding to the C—S—H structure) and indirectly (through removal of the structurally weak CH inclusions). Additionally, HAP is much more resistant to environmental effects than CH, rendering CPSC more corrosion resistant that OPC. Additionally, the presence of HAP or other phosphate inclusions within the cement structure brings enhanced bio-compatibility and bio-activity. It should be noted that it is not possible to achieve a similar combination of properties by mechanical mixing of OPC (or similar cement) with the hydroxyapatite or other calcium phosphates; this is because in CPSC the two principal components (C—S—H and HAP) co-precipitate (in the composition of the present invention) to form a unique microstructure having a high-degree of homogeneity on a level of approximately 100 nm.

Since the CPSC is on average twice as strong in compression as compared to non-modified ordinary Portland Cement (OPC), one embodiment of the invention provides a method for using the CPSC hydraulic cement compositions for structural applications. In these types of applications the high mechanical strength, adjustable setting time, and stability to against the corrosions and heat are of primary importance. Consequently, the CPSC cement compositions of present invention can be used for making high strength mortar, concrete, and other materials common in the construction industry.

Furthermore, since the CPSC converts a substantial amount of the CH resulting from hydration of the calcium silicates into bio-compatible and bio-active calcium phosphates, the present invention also provides methods for the use of CPSC for medical devices, such as prostheses, implants, and other surgical procedures. As noted above, the calcium phosphate, (particularly hydroxyapatite) renders the cement bioactive, biocompatible, and durable; in addition, the removal of CH through HAP formation lowers the pH of the mix, which makes CPSC more compatible with the living tissue. These characteristics also make the cement particularly useful for dental cements, such as dental root-end filling material, retrofilling materials, pulp capping, apexification, and for sealing of perforations.

These and other features and advantages of the present invention will be more fully understood from a reading of the following detailed description with reference to the accompanying drawings.

DETAILED DESCRIPTION

The present invention provides novel cement compositions and methods of making them, and for using them in variety of application fields, ranging from engineering and construction uses to medical/dental implants and fillings. The novel Calcium Phosphate Silicate Cement (CPSC) of present invention has relatively high early strength and relatively high overall compressive strength (as compared to OPC setting at similar conditions for the same time), adjustable setting time, low hydration heat, resistance to degradation, high bioactivity and biocompatibility, and stability to against corrosive environments.

The CPSC is obtained through a chemical process of in-situ formation (co-precipitation) of hydroxyapatite/calcium silicate hydrate gel composite at room- or nearly room-temperature and pressure, accompanied by the removal of CH during cement hydration. This is accomplished by reacting the CH in-situ with phosphate ions to precipitate much stronger and chemically resistant calcium phosphate, in particular hydroxyapatite (HAP), that is intimately mixed with the C—S—H gel. The resulting composite cement has high mechanical strength, but also biocompatibility, bioactivity, and adjustable setting time. These properties do not require application of hydrothermal treatment or pressure-assisted forming of the components.

The major components of the CPSC cement compositions of the present invention, which normally make up approximately 60% by weight of cement in the cement composition, are at least one calcium silicate compound and at least one phosphate compound. Suitable calcium silicate compounds include, but are not limited to, dicalcium silicate C2S (2CaO.SiO$_2$), tricalcium silicate C3S (3CaO.SiO$_2$) and mixtures thereof. Tetracalcium silicate C4S (4CaO.SiO2) may also be used. The calcium silicate compound may constitute between 10-99% of the cement composition by weight, and is preferably in the range from about 40-80% of the composition by weight.

Suitable phosphate compounds include but are not limited to, calcium phosphates (including mono-calcium phosphate, di-calcium phosphate,and mixtures thereof), magnesium phosphates, sodium phosphates, zinc phosphates, aluminum phosphates, iron phosphates, potassium phosphates, nickel phosphates, zirconium phosphates, phosphoric acid, organo-metallic phosphates, and mixtures thereof. Mono-calcium phosphate (calcium phosphate monobasic) is generally preferred. The phosphates used in present invention may contain hydration water. More complex (pre-reacted) phosphates may also be used. In addition to mono-phosphate ($PO_4^{-3}$) compounds di-phosphate ($P_2O_7^{-4}$) compounds tri-phosphate ($P_3O_{10}^{-5}$) compounds, meta-phosphate compounds, and mixtures thereof, may be used). The phosphate compound is included in an amount sufficient to react a major poriton of the calcium hydroxide produced during hydration of the cement to form hydroxyapatite or other calcium phosphates. The phosphate may be included in an amount within the range from about 1-70% by weight of the cement composition, with 5-30% being preferred; a range of about 10-15% has been found particularly suitable, especially when using mono-calcium phosphate.

The minor or ancillary components of the cement compositions of the present invention may include, but are not limited to, silicon dioxide, tricalcium aluminate (3CaO.Al$_2$O$_3$), tetracalcium aluminoferrite (4CaO.Al$_2$O$_3$.Fe$_2$O$_3$), calcium sulphate, calcium sulfate dihydrate (CaSO$_4$.2H$_2$O), and mixtures thereof, which typically make up less than about 30% by weight of the cement composition. Also, the cement may contain a number of impurity oxides which are present in the original raw materials, which will normally make up less than about 15% by weight of cement composition, including, but not limited to, iron oxides, magnesia (MgO), potassium oxide, sodium oxide, sulfur oxides, carbon dioxide, water, and mixtures thereof.

Calcium compounds may be included, including but not limited to, calcium oxide, calcium carbonates, calcium hydroxides, and mixtures thereof.

When water is mixed with the cement compositions, a complicated set of reactions is initiated. The phosphate and calcium compounds quickly dissolve in water and precipitate to produce new calcium phosphate compounds, principally hydroxyapatite when the pH is above 7.0. The reaction speed is adjustable in range from 20 minutes to 2 days according to the needs of the application, through minor changes in the system chemistry and precursor morphology.

Initially, the calcium silicates react with water to produce a calcium silicate hydrate gel (CaO—SiO$_2$-H$_2$O gel); however, the rate of the hydration reaction of the calcium silicates is slower than the rate of the formation of the hydroxyapatite. Consequently, in this process of co-precipitating, nano-size particles of calcium silicate hydrate gel fill the voids among the precipitating hydroxyapatite particles.

A key feature of the present invention is the ability for in-situ formation through co-precipitation of hydroxyapatite/calcium silicate hydrate gel composite at room temperature, in ordinary prepared cement paste, without a need for increased pressure or temperature, and in particular without a need for hydrothermal treatment of the setting cement paste. The formation of C—S—H/HAP composite is accompanied by a decrease of CH content in the set cement (CH being the weakest component of the set cement, structurally and chemically). The resulting CPSC material exhibits significantly increased mechanical strength, wherein the calcium phosphate and hydroxyapatite act as a reinforcement phase and the calcium silicate hydrate gel is a matrix in the composite structure.

Reactions

The precipitation reaction (A) of calcium phosphate apatite is as follows:

$$10Ca^{2+} + 6PO_4^{3-} + 2OH^- \rightarrow Ca_{10}(PO_4)_6(OH)_2 \tag{A}$$

where Ca/P ratio is between 1.2 and 2.0.

The hydration reactions (B, C) of calcium silicates can be approximated as follows:

$$2[3CaO.SiO_2] + 6H_2O \rightarrow 3CaO.2SiO_2 + 3H_2O.3Ca(OH)_2 \tag{B}$$

$$2[2CaO.SiO_2] + 4H_2O \rightarrow 3CaO.2SiO_2.3H_2O + Ca(OH)_2 \tag{C}$$

where the calcium hydroxide CH is the hydration product which ordinarily contributes to the high alkalinity of the cement. It is widely recognized that the calcium silicate hydrate is not a well-defined compound and formula of (3CaO.2SiO$_2$.3H$_2$O) is only an approximate description. The ratio of CaO/Si$_2$O is in between 1.2 and 2.3, which depends on water contain, aging time and temperature, and other factors. The high pH=10-12 during hydration, in presence of phosphate ions $PO_4^{3-}$ increases the precipitation rate of the calcium phosphate, preferably hydroxyapatite, according to the reaction (A), which in turn decreases the overall alkalinity of hydration. Consequently, a new process is created wherein we both (i) decrease the alkalinity and CH content in setting cement; and (ii) provide a strong and bio-active HAP phase which reinforces the composite.

In order to further remove the calcium hydroxide CH during setting of the cement, and therefore further enhance its mechanical strength, additional phosphate may be introduced into the cement composition, which will continue to react with calcium hydroxide to form hydroxyapatite. If the calcium phosphate compound is calcium phosphate monobasic in the cement, the following dynamic chemical reaction takes place:

$$3Ca(H_2PO_4)_2 + 7Ca(OH)_2 \rightarrow Ca_{10}(PO_4)_6(OH)_2 + 12H_2O \quad (D)$$

The calcium hydroxide, produced during the hydration reaction of calcium silicates, reacts relatively rapidly with the phosphate compounds to produce a new compound, hydroxyapatite HAP. Importantly, the same reaction (D) also provides water, which continues to react with the calcium silicates. The water supplied through the dynamic reaction (D) is one of the most important factors to control the hydration reaction speed, and thus the setting time, hardening time, and the final mechanical strength of the composite CPSC.

To further improve mechanical strength, silica fume, or any other form of silica, e.g. sol-gel derived silica, may be introduced into the cement composition to react with remnant calcium hydroxide to produce the amorphous calcium silicate hydrate gel, and therefore further decrease the CH content and alkalinity of the cement.

The hydration rate of the calcium silicates (reactions B, C) is increased in the CPSC composition, since the phosphate compounds react with calcium hydroxide to produce hydroxyapatite and water (reaction D), thus shifting the equilibrium. Therefore, the setting and hardening time of CPSC cement is shortened.

The hydration reactions of calcium silicates normally result in a pH over 12 in ordinary cement compositions. In the present invention, the phosphate compounds react with calcium hydroxide and thus neutralize pH of the cement. The calcium hydroxide is therefore only the intermediate product of the hydration reaction of calcium silicates in CPSC cement.

In ordinary Portland cement (OPC), the calcium silicate hydrate C—S—H is an amorphous or poorly crystalline material which forms very small particles in the of submicron size (less than 1 um in any dimension). C—S—H is the main strength-providing compound in OPC. The calcium hydroxide is a well-crystallized material with a definite stoichiometry, which occupies about 20-25% of the volume of set OPC cement paste. The calcium hydroxide precipitates where free space is available and in extreme cases may completely engulf the cement grains. However, calcium hydroxide is mechanically weak and reduces the mechanical strength and chemical resistance of the cement. As noted above, in the present invention the calcium hydroxide is only an intermediate product of hydration reactions B, C, since it reacts with the phosphate compounds to produce the hydroxyapatite and water according to reactions A, D. Consequently, the decreased content of CH in the set CPSC provides a relative increase in strength and chemical resistance of the cement.

In set CPSC, the calcium silicate hydrate interlocks with the hydroxyapatite or other calcium phosphate, leading to in situ formation of the composite-like structure on a nano-scale level. The hydroxyapatite is the reinforcement phase and calcium silicate hydrate is the matrix of the composite structure. Both phases provide mechanical strength to the composite. In comparison with ordinary Portland cement (OPC), the mechanical strength and corrosion resistance of present cement CPSC are therefore significantly improved, because weak phase calcium hydroxide is replaced with the high strength and chemically stable hydroxyapatite.

One use of the hydraulic CPSC cement of the present invention is thus for structural applications, because of its (i) relatively high mechanical strength, (ii) adjustable setting time, (iii) chemical stability, and (iv) low alkalinity. Consequently, the CPSC cement composition of the present invention can be used for making high strength concrete for block making, reservoirs, pre-cast operations, high structural concrete (bridge, high-rise buildings, dams, and nuclear powder plants), plaster and mortar, and for use in mining operations, and many other structural and non-structural applications. The significantly less alkaline character of CPSC (as compared to OPC) makes it more suitable for use in combination with alkaline-sensitive materials, such as some metals, polymeric/organic components, and additives. Many other uses of such high-strength cement and concrete may be envisaged.

Hydroxyapatite (HAP) is the major inorganic component, and an essential ingredient, of normal human bone and teeth. The compressive strength of hydroxyapatite (>60 MPa) is much higher than that of calcium hydroxide (<1 MPa). Hydroxyapatite ($Ca_{10}(PO_4)_6(OH)_2$) is one of the most biocompatible and bioactive ceramics because it is similar to the mineral constituents of human bone and teeth. Due to the relatively large content of HAP, the CPSC cement of the present invention is not only bioactive and biocompatible, but also is osteoinductive and osteogenic (encourages bone in-growth).

Another use of the CPSC cement of the present invention is therefore for medical and dental materials and devices, such as prostheses, implants, fillings, coatings, and other surgical procedures. This is because of high content of HAP The CPSC cement is self-setting, injectable, and of high strength, allowing it to be used for both weight and non-weight bearing applications. The cement resists disintegrative washout upon contact with blood, and injection into the wound is less stressful to the surrounding tissue because of it being biocompatible with the physiological environment. The CPSC is not resorbed (dissolved) in contact with living tissue in body fluids.

Bio-medical applications of the CPSC cement of the present invention include, but are not limited to, percutaneous vertebroplasty, craniomaxillofacial surgery applications, ridge augmentation, spinal fusion cage/implant, treatment of radial fractures, treatment of temporal mandibular, joint disorders, plastic surgery and cosmetic augmentation, bone graft substitutes, veterinary applications, and drug delivery. Other examples include biological use of CPSC or CPSC-based composites with drugs or proteins to address specific medical problems; for example microspheres of CPSC may be designed for targeted delivery of drugs, proteins, DNA, or other medically active species to the area of interest in the body. Examples of dental applications include, but are not limited to, dental root-end filling material, retrofilling materials, pulp capping, apexification, and sealing of perforations.

The CPSC cement of the present invention can also be used for making composite materials, including specific secondary reinforcement phases, such as fibers, aggregates, bioglasses, bioceramics, polymers, and metals, in variety of morphological forms such as particles, fibers, loops, and others.

In comparison with mineral trioxide aggregate (MTA), the CPSC cement of the present invention has higher mechanical strength and is more bioactive and biocompatible. The setting rate of CPSC is adjustable, thus making it more attractive for dental operations. Since the phosphate compound in CPSC cement composition neutralizes the calcium hydroxide and thus lowers the pH from over 12 to around 8-11 during the hydration reaction, CPSC is more friendly to the surrounding tissues. Radiopaque components may be added to render the CPSC radiopaque for the purposes of dental diagnostics. Suitable radiopaque substances are generally selected from heavy metals, oxides of heavy metals, salt of heavy metals, and mixtures thereof. For example, zirconia ($ZrO_2$), tantalum oxide ($TaO_2$), Barium sulfate ($BaSO_4$), and Bismuth oxide ($Bi_2O_3$) are radiopaque materials suitable for such applications; other suitable material include the heavy metals gold, silver, barium, bismuth and tantalum; mixtures of the foregoing may also be used. The radiopaque substance may be included in an amount within the range from about 3-50% by weight of the cement composition, preferably in an amount within the range from about 10-30%.

The presence of the phosphate compounds that consume CH produced in the calcium silicates hydration reactions also shifts the equilibrium and therefore affects the overall kinetics of the setting process. Namely, the dynamic chemical reactions of calcium silicates hydration are speeded up since the phosphate compounds in cement compositions react with calcium hydroxide to produce hydroxyapatite and water. Therefore, the setting and hardening time of the cement decreases. These parameters of the setting reaction are affected by the concentration and solubility of the phosphate compounds added to the regular hydraulic cement, such as Portland cement. Therefore, a new method for controlling the setting reaction dynamics, and therefore the release heat and shrinkage, is provided.

It is also important to emphasize that production of the Portland cement is one of the most energy-consuming and polluting (e.g. in terms of carbon dioxide $CO_2$ released) processes known to humanity. As billions of tons of the cement are produced annually, any advance over OPC that retains or improves its properties (such as strength and corrosion resistance) while replacing part of the cement with other compounds, as does the present invention, may significantly decrease the negative environmental impact of cement production.

Test Results

Figure 1:
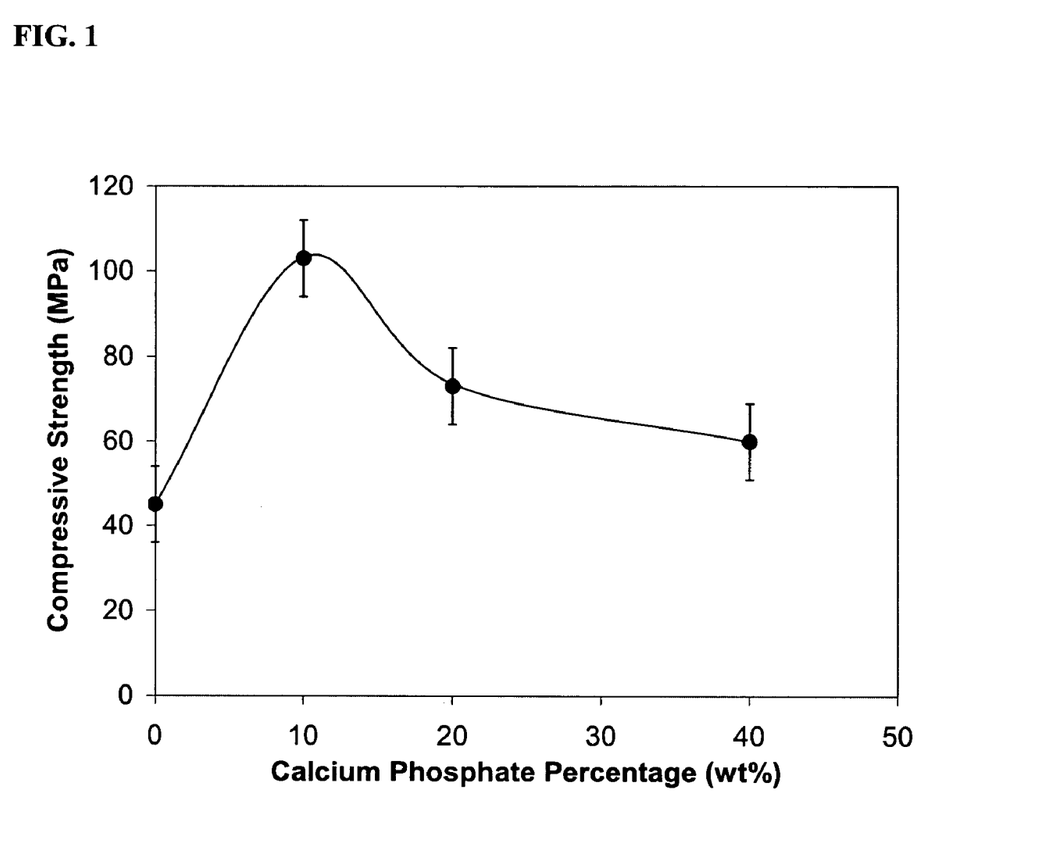
FIG. 1 is a graph illustrating compressive strength of Portland cement modified to produce CPSC in accordance with the present invention, showing the compressive strength as a function of the calcium phosphate content of the cement.

FIG. 1 illustrates compressive strength of a CPSC cement in accordance with the present invention as a function of calcium phosphate content. By adding 10-15 wt % calcium phosphates into the Portland cement to result in CPSC cement, the compressive strength of is significantly increased, from about 45 MPa to about 103 MPa (for 7 days setting time).

Figure 2:
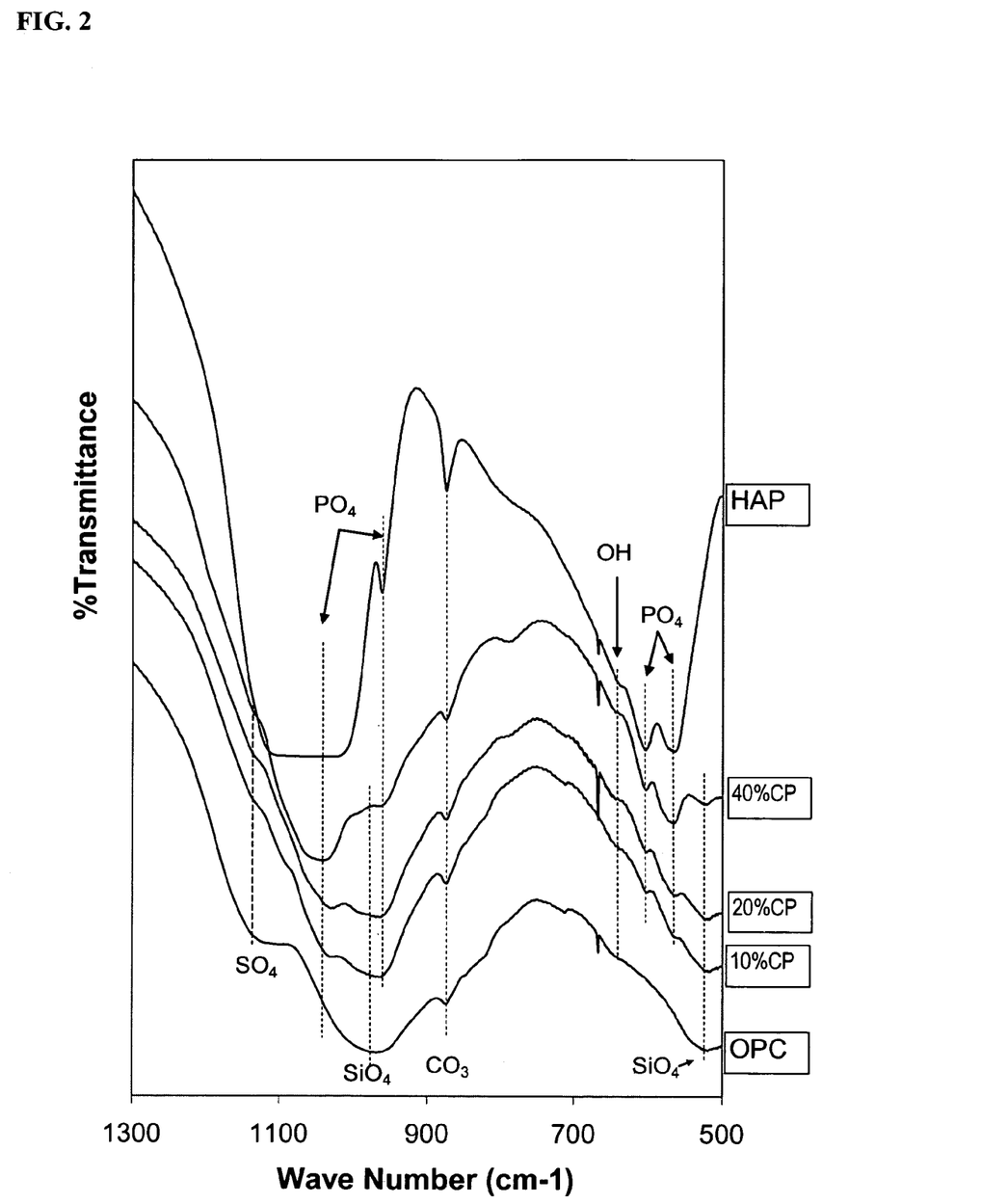
FIG. 2 is a graph of FTIR spectra of OPC and of cement compositions in accordance with the present invention having varying percentages of calcium phosphate.

FIG. 2 illustrates FTIR spectra of reference samples of ordinary Portland cement (OPC) and the hydroxyapatite HAP, and of the CPSC cement compositions produced through combination of OPC with different percentages of calcium phosphate compounds. When water is mixed with the CPSC cement, a complicated set of reactions is initiated. The calcium silicates react with water to produce a calcium silicate hydrate gel ($CaO-SiO_2-H_2O$ gel, or C—S—H, as commonly represented in literature) which provides the strength, and calcium hydroxide (CH) which contributes to the alkalinity of the cement, but is also a weak link of the cement. There are three main regions related to the vibration frequencies of $SO_4$, $SiO_4$, and $CO_3$ groups in wave number ranges 500-1300 $cm^{-1}$. For the OPC samples, the sulfate absorption bands (i.e. the S—O stretching bands) at 1150-1100 cm in hydrated Portland cement are shown as a shoulder band. The bands at 960 $cm^{-1}$ and 520 $cm^{-1}$ are contributed by the Si—O asymmetric stretching and the Si—O out-of-plane bending vibration of $SiO_4$ group of calcium silicate hydrate gel. Another band at 870 $cm^{-1}$ is contributed by the vibration of $CO_3$ group (refer also to the Mollah et al, "A Fourier transform infrared spectroscopic investigation of the early hydration of Portland cement and the influence of sodium lignosulfonate" *Cement and Concrete Research* 30 (2000) 267-273).

For the hydroxyapatite reference sample (HAP), the absorption spectrum of HAP has three main regions related to the vibration frequencies of the $OH^-$, $PO_4^{3-}$ and $CO_3^{2-}$ ions (Vaidya, et al, Pressure-induced crystalline to amorphous transition in hydroxylapatite, *J. Mater. Sci.*, 32 (1997) 3213-3217). The absorption of the internal stretching of OH in hydroxyapatite is located at 630 $cm^{-1}$. The vibration of the phosphate ion are an asymmetric stretch (1100-1028 $cm^{-1}$), a degenerate symmetric stretch (960 $cm^{-1}$), and a double degenerate asymmetric bend (600 $cm^{-1}$ and 560 $cm^{-1}$). The $CO_3^{2-}$ has vibration band at 870 $cm^{-1}$. This is a typical amorphous or poor crystallinity structure hydroxyapatite.

In comparison with OPC, the frequencies of bands of vibration and liberation modes of various functional groups of hydroxyapatite do appear on FTIR spectra by adding 10 wt % calcium phosphate compounds. The intensity of absorption bands increases with increasing content of calcium phosphate compounds. This indicates formation of hydroxyapatite in the CPSC cement composition.

Figure 3:
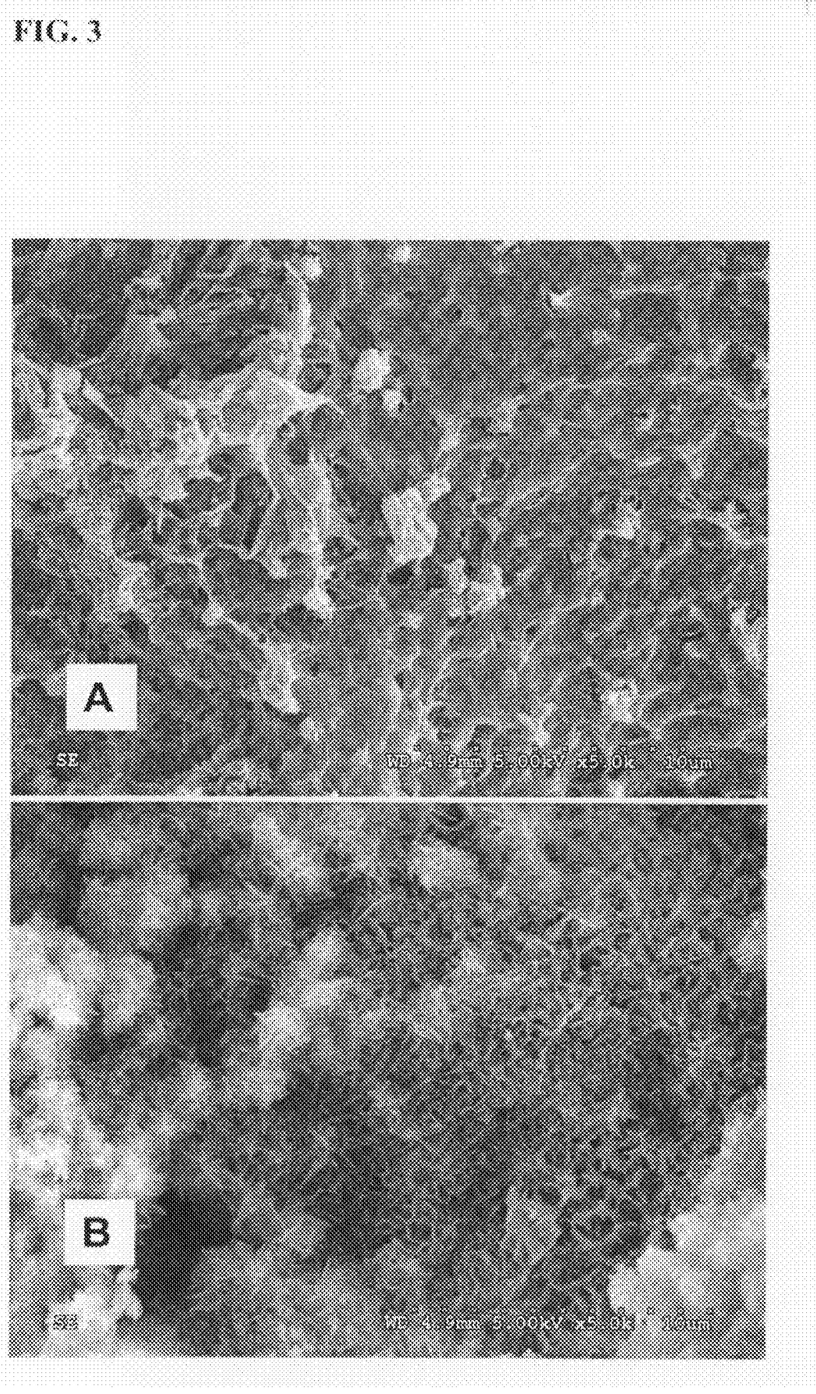
FIG. 3 is a set of electron microscope scans providing side-by-side comparison of the results of bio-activity tests conducted for ordinary Portland cement and a CPSC cement in accordance with the present invention having a calcium phosphate content of about 20%, at 5,000× magnficiation.

FIG. 3 illustrates the results of bioactivity tests conducted for (A) ordinary Portland cement (OPC) and (B) CPSC cement with approximately 20% of the calcium phosphates co-precipitated with C—S—H gel. All samples were immersed in SBF (Simulated Body Fluid) solution at 37° C. for 10 days, and then the samples were washed with distilled water and dried for scanning electron microscope (SEM) observations. There is no hydroxyapatite formation observed on surface of ordinary Portland cement OPC by SEM (although traces of other calcium phosphates may be observed under higher magnification and/or longer exposure to SBF; this weak effect was also reported for the OPC-like mineral trioxide aggregate (MTA) utilized for dental cements), which indicates that the OPC is not bioactive or only weakly bioactive. A typical hydroxyapatite structure layer is formed on the surface of CPSC cement indicating that the cement of the present invention has high bioactivity.

Figure 4:
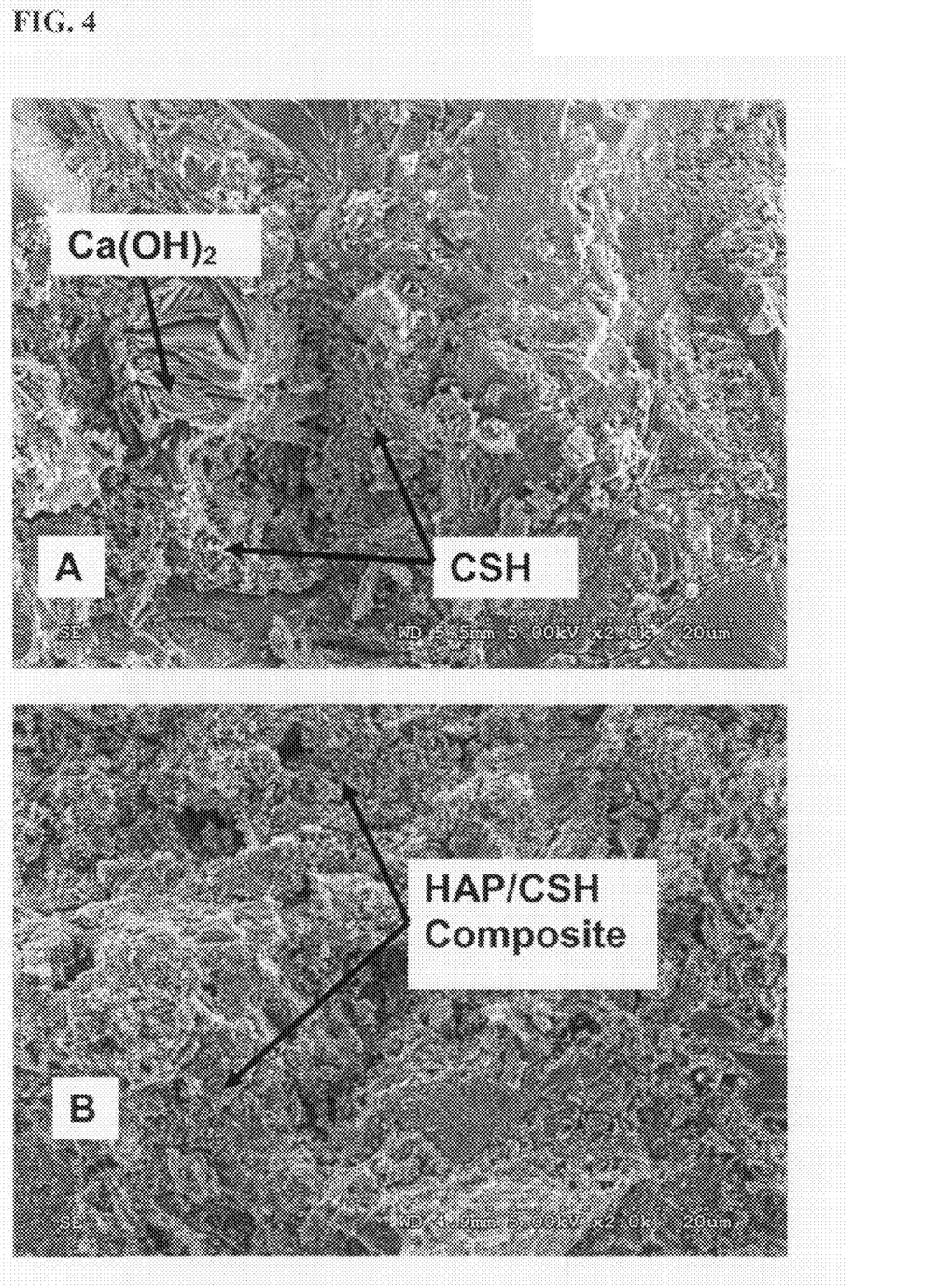
FIG. 4 is a set of electron microscope scans providing side-by-side comparison of the microstructures of the fracture surfaces of ordinary Portland cement and of a CPSC cement in accordance with the present invention, at 2,000× magnification.

FIG. 4 illustrates the microstructures of fracture surfaces of (A) ordinary Portland cement and (B) CPSC, at 2000× magnification. Scan (A) clearly shows relatively large $Ca(OH)_2$ crystals; the calcium hydroxide does not form homogenous crystals in the cement paste, but rather grows into the free space, such as pores and voids. By contrast, large $Ca(OH)_2$ crystals are absent in the calcium phosphate silicate cement, as illustrated in Scan (B); instead, a composite of HAP/C—S—H can be observed on this surface. The in-situ formation of HAP/C—S—H composite was confirmed by elemental mapping through Energy Dispersive X-ray (EDX) analysis.

Figure 5:
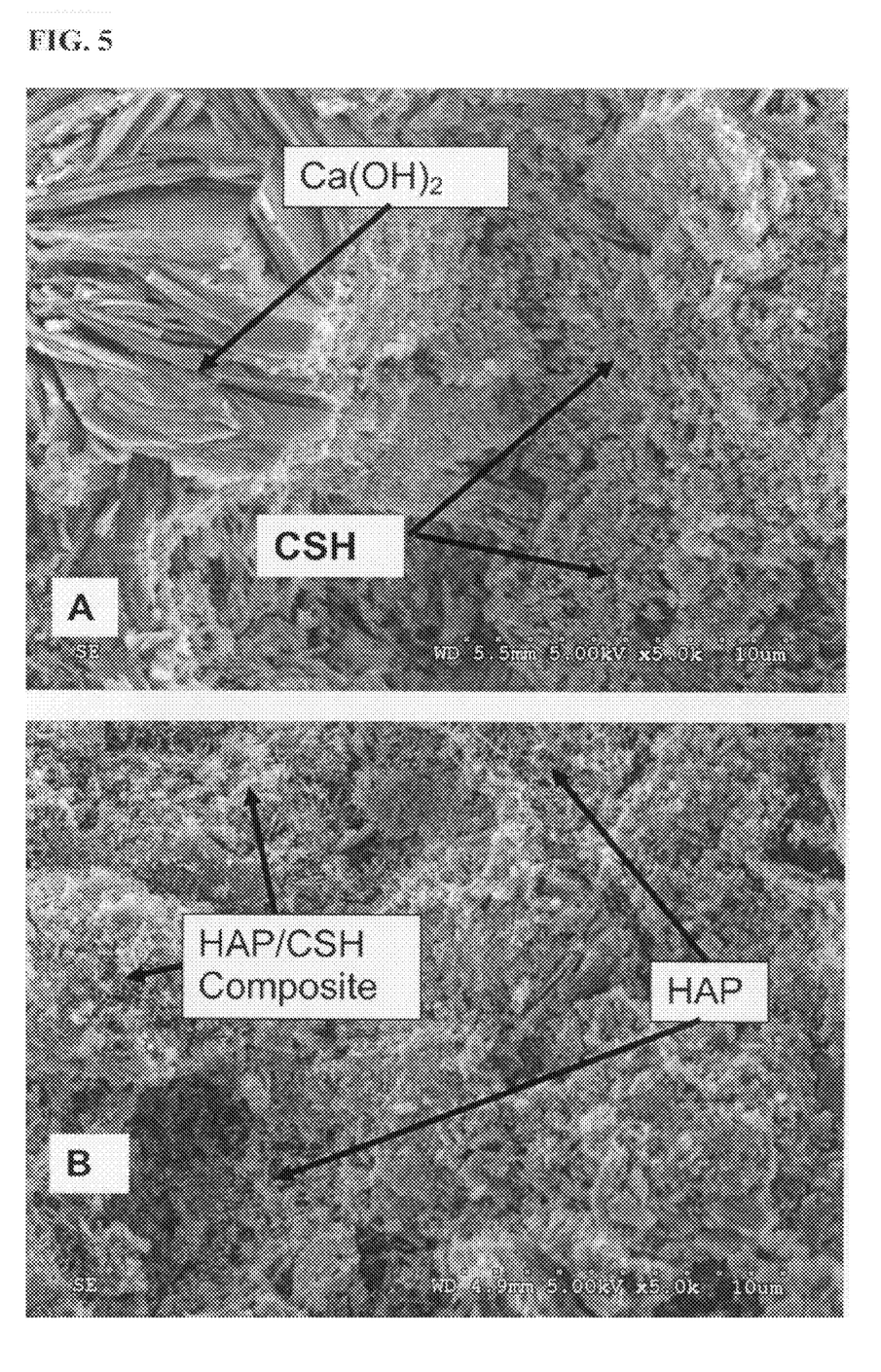
FIG. 5 is a set of electron microscope scans providing side-by-side comparison of the microstructures of the fracture surfaces ordinary Portland cement and a CPSC cement in accordance with the present invention, at 5,000× magnification.

FIG. 5 illustrates the microstructures of the fracture surfaces of (A) ordinary Portland cement and (B) CPSC at 5000× magnification. Scan (A) shows the crystal structure of $Ca(OH)_2$ and calcium silicate hydrated gel (CSH). The pure HAP phase and HAP/CSH composite was observed in the CPSC sample as shown by Scan (B) which was confirmed by EDX analysis.

Figure 6:
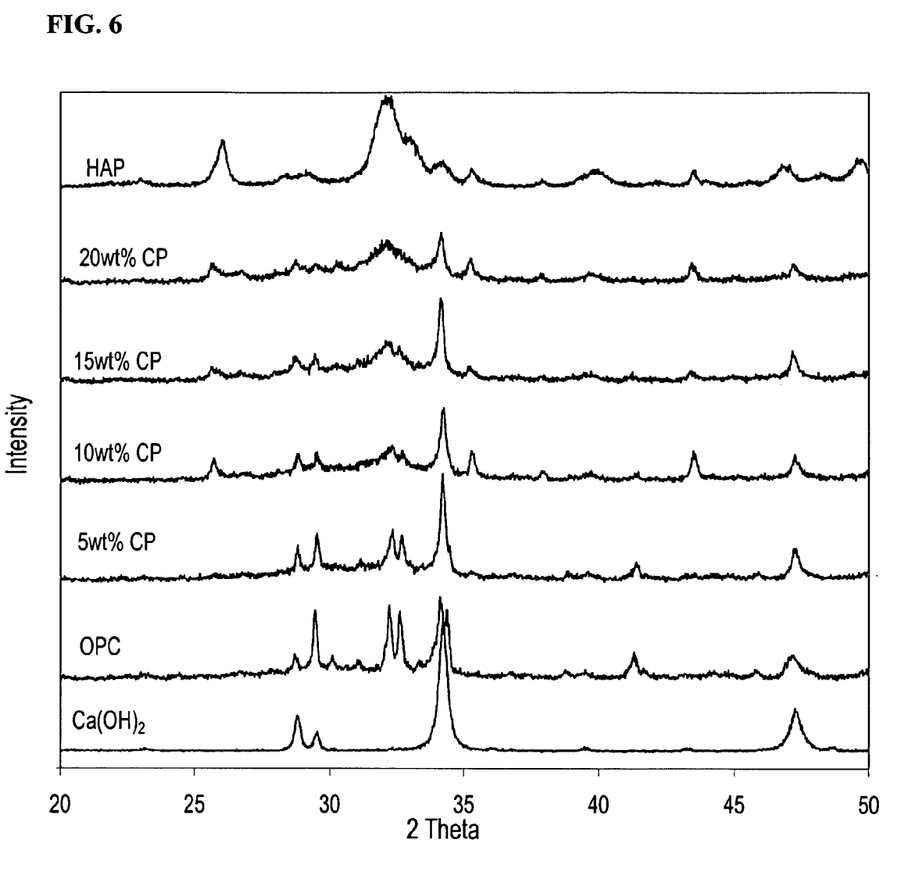
FIG. 6 is a graph of x-ray defraction patterns obtained for ordinary Portland cement, for CPSC formed by modification of Portland cement in accordance with the present invention, and for pure calcium hydroxide and pure hydroxyapatite as references.

FIG. 6 illustrates X-ray diffraction patterns for the OPC, and for Portland cement with calcium phosphate added so as to form CPSC. Additionally, for reference, the bottom pattern is from pure calcium hydroxide CH and the top pattern is from pure amorphous or poorly crystallized hydroxyapatite (i.e. the type of HAP formed during the dissolution-precipitation setting reaction of CPSC). The hydroxyapatite diffraction peak at 32.3 degree of 2-Theta angle starts to appear after adding 10 wt % of the calcium phosphate (CP) precursors into OPC. Simultaneously the relative intensity of the X-ray diffraction peaks of calcium hydroxide decrease with the increase of the calcium phosphate content in the OPC (i.e. compare the decrease of $Ca(OH)_2$ peak intensity at about 47.5

Two-Theta). This X-ray diffraction pattern indicates that the calcium phosphate additive dissolves in water, reacts with calcium hydroxide (which is the hydration product of calcium silicates of OPC) and subsequently co-precipitates the hydroxyapatite, in intimate mixture with the co-precipitating C—S—H gel.

EXAMPLES

Example 1

Preparation and Properties of Phosphate Silicate Cement CPSC

This example used general purpose commercial ordinary Portland type cement OPC (ASTM I) containing approximately 50% C3S, 25% C2S, 12% C3A (tricalcium aluminate $3CaO.Al_2O_3$), 8% C4 AF (tetracalcium aluminoferrite $4CaO.Al_2O_3.Fe_2O_3$), and 5% calcium oxide CaO. 11 grams of dicalcium phosphate was dried in the furnace at 140° C. for 24 hours and then mixed with 29 grams of the tetracalcium phosphate and with the OPC cement powder (160 grams) in alcohol solution by ball milling for 24 hours. The resulting slurry was spray dried. The average particle size of the cement powder was about 10 um. The setting time of the CPSC cement thus was about 2 hours, for a water/cement ratio of 0.21. The average compressive strength after 7-day incubation at 37° C. and 100% humidity was 104 MPa, with a standard deviation of 7 MPa, (FIG. 1). The X-ray diffraction pattern provided in FIG. 6 indicates that the set cement contained about 15% of HAP, and about 8% of $Ca(OH)_2$.

These results compared favorably with the characteristics of the control samples of the OPC material, hydrated under identical conditions. The average compressive strength of the OPC was 45 MPa, with a standard deviation of 5 MPa, (FIG. 1). The X-ray diffraction pattern in FIG. 6 indicates that the set cement contained no HAP, and about 20% of $Ca(OH)_2$. The scanning electron microscope microstructures shown in FIGS. 4, 5A (OPC) and FIGS. 4, 5B (CPSC) clearly indicate the composite character of the CPSC, and the decreased content of CH in the CPSC.

Example 2

Preparation of High Strength CPSC Cement for Orthopedic Applications

In this example the phosphate silicate cement was prepared synthetically using well defined pure chemicals (as opposed to the poorly defined minerals utilized for preparation of typical commercial Portland cement). The raw materials used for the preparation of CPSC cement were colloidal silica (50 wt % Ludox, from 3M company) for $SiO_2$, calcium hydroxide (99.9%, Sigma-Aldrich) for CaO, tetracalcium phosphate ($Ca_4(PO_4)_2O$), and dicalcium phosphate anhydrate ($CaHPO_4.H_2O$) (Fisher). Alternatively, and with no effect on the final properties of CPSC, the colloidal silica may be derived from thermal decomposition of hydrated silicon alkoxide such as tetra-eth-oxide silicate (TEOS).

The designed composition of the present cement is 65 wt % tricalcium silicate, 20 wt % dicalcium silicate, 10 wt % tetracalcium phosphate, and 5 wt % dicalcium phosphate. A 200 g batch was prepared by mixing 96.32 g of colloidal silica, 160.98 g calcium hydroxide, and 300 g distilled water in an alumina jar, and ball milling for 24 hours. The slurry mixture was dried by using a spray dryer, and was then fired in a high temperature furnace at 1550° C. for 1 hour to form tricalcium silicate and dicalcium silicate, followed by natural cooling to room temperature. The resulting cement clinker was ground to −325 sieve particle size (<45 um particle size), with an average particle size of about 10 um. 11.25 g of dicalcium phosphate anhydrate was dried in the furnace at 140° C. for 24 hours and then mixed with 20 g of the tetracalcium phosphate and combined with the fired cement powder (168 grams) in alcohol solution by ball milling for 24 hours. The resulting slurry was spray dried. The average particle size of the cement powder was about 10 um. The setting time was about 4 hours. The average compressive strength after 7-day incubation at 37° C. and 100% humidity was 101 MPa, with a standard deviation of 8 MPa. The control samples of the cement without the addition of phosphates, and set under identical conditions, had average compressive strength 45 MPa, with a standard deviation of 5 MPa.

The X-ray diffraction pattern provided in FIG. 6 indicates that the set CPSC cement contained about 15% of HAP. This cement paste was injectable and suitable for orthopedic applications.

Example 3

Preparation of CPSC High Strength Gray and White Cements for Dental Applications The following procedure is to prepare a high strength, pure, bioactive, and biocompatible CPSC cement for dental applications. Raw materials used are colloidal silica (50 wt % Ludox, 3M) for $SiO_2$, calcium hydroxide (99.9%, Sigma-Aldrich) for CaO, boehmite (AlOOH) for $Al_2O_3$, iron oxide ($Fe_2O_3$, 99% Fisher), calcium sulfate dehydrate ($CaSO_4.H_2O$, 99%, Fisher), $Ca(OH)_2$, and monocalcium phosphate ($Ca(H_2PO_4)_2$, 99%, Sigma). Alternatively, and with no effect on the final properties of CPSC, the colloidal silica may be derived from thermal decomposition of hydrated silicon alkoxide such as tetra-eth-oxide silicate (TEOS).

The designed composition of the cement is 58 wt % tricalcium silicate ($3CaO.SiO_2$), 11 wt % dicalcium silicate ($2CaO.SiO_2$), 6 wt % tricalcium aluminate ($3CaO.Al_2O_3$), 7 wt % tetracalcium aluminoferrite ($4CaO.Al_2O_3.Fe_2O_3$), 4 wt % calcium sulfate dehydrate ($CaSO_4.2H_2O$), 4 wt % calcium oxide, and 10 wt % monocalcium phosphate ($Ca(H_2PO_4)_2$). A 200 g batch was prepared by mixing 78 g colloidal silica, 156.9 g calcium hydroxide, 10.57 g boehmite, 4.61 g ferrite oxide, and 300 g distilled water in alumina jar, and ball milled for 24 hours. The slurry mixture was dried by using a spray dryer, and then was fired in a high temperature furnace at 1550° C. for 1 hour, and then cooled naturally to room temperature, followed by grinding to about 10 um average particle size. 20 g of monocalcium phosphate, 8 g of calcium hydroxide, and 8 g of calcium sulfate dehydrate were mixed with the fired cement powder in alcohol solution by ball milling for 4 hours. The slurry was dried by using spray dryer.

The setting time of the CPSC cement prepared as described above was around 6 hours, for a water/cement ratio of 0.21. The compressive strength after 7-day incubation at 37° C. and 100% humidity was 110 MPa, with a standard deviation of 7 MPa. The control samples of the cement without the addition of phosphates, and set under identical conditions, had on average compressive strength of 48 MPa, with a standard deviation of 4 MPa. The X-ray diffraction pattern provided in FIG. 6 indicates that the set CPSC cement contained about 15% of HAP.

This CPSC cement paste was injectable, of gray color, and suitable for dental applications, such as root-end filling material, retrofilling materials, pulp capping, apexification, and most importantly the sealing of perforations. For making white color CPSC cement for the specific dental applications requiring color control (e.g. for cosmetic reasons), the process was repeated exactly, except that the iron oxide was excluded from the cement composition. The properties of such white variant of CPSC were essentially the same as the properties of the gray variant of the CPSC.

Example 4

In Vitro Testing of Bioactivity of the CPSC Cements

This example compares the bioactivity of ordinary Portland cement (OPC) to that of the CPSC cement with 10% calcium phosphate. Both cement powders were prepared by the process described in Example 3, for the "gray" cement containing iron oxide, either without phosphates (control sample, OPC) or with phosphates (CPSC). The paste samples were prepared by mixing the cement powder with distilled water at the ratio of water/cement w/c=0.25. The cement paste was filled into cylinder mold of 1 inch diameter and 2 inch height. The samples were incubated at 100% humidity and without use of any organic species, and its pH was adjusted to 7.4 with 7.5% $NaHCO_3$ solution (Li, et al, Apatite formation induced by silica gel in a simulated body fluid. *J Am Ceram Soc* 75 (1992), pp. 2094-2097). All samples were immersed in the SBF solution at 37° C. for 10 days, and then the samples were washed with distilled water and dried for SEM observations as illustrated in FIGS. 4-5.

No hydroxyapatite formation was observed on the surface of ordinary Portland cement by SEM, thus indicating that the OPC is not bioactive. However, a hydroxyapatite structure layer was found on the surface of the CPSC cement disclosed of the present invention, indicating good bioactivity, osteoinductivity, and osteogenicity.

Example 5

CPSC Cement Composition with Radio-Opaque Component for Dental Applications

This example illustrates the procedure for making CPSC dental cement with radio-opaque material. The fired cement powders were prepared as described in Example 3. Zirconia ($ZrO_2$, Zircoa, USA) was chosen as the radio-opaque material for dental application because zirconia is biocompatible and used for orthopedic implant devices. Alternatively, and with no effect on the final properties of CPSC, the radio-opaque material may be derived from tantalum oxide $TaO_2$. 80 g of the CPSC cement powder and 20 g of zirconia were mixed with powder/powder mixer for 20 min. X-ray tests indicated clear visibility of the modified CPSC cement, demonstrating that the dental cement with zirconia radio-opaque is suitable for dental applications.

Example 6

Effect of Phosphate Compound on Mechanical Strength

This example further demonstrates that the compressive strength of Portland cement was significantly improved by adding phosphate compounds to result in CPSC. The composition of ordinary Type I Portland cement used for the testing was about 50 wt % tricalcium silicate ($3CaO.SiO_2$), 25 wt % dicalcium silicate ($2CaO.SiO_2$), 12 wt % tricalcium aluminate ($3CaO.Al_2O_3$), 8 wt % tetracalcium aluminoferrite ($4CaO.Al_2O_3.Fe_2O_3$), and 5 wt % calcium sulfate dehydrate ($CaSO_4.2H_2O$). The dicalcium phosphate and calcium oxide (weight ratio of DCP/CaO=2:3) was introduced to the Portland cement composition in the amounts of 0 wt %, 10 wt %, 20 wt %, and 40 wt % and mixed in alcohol solution by ball milling for 4 hours, and then dried in oven at 70 C for 12 hours. The mixture of cement powder was mixed with distilled water at w/c=0.25. The cement paste was filled into cylinder molds of 1 inch diameter and 2 inch height. The samples were incubated at 100% humidity at room temperature for seven days. The cylinder samples were used to determine the maximum compressive strength with an Instron Universal Testing Machine with a cross-head speed head of 2 mm/min. The samples were further characterized for phase content by SEM and X-ray diffraction. The results are illustrated in FIGS. 4, 5, and 6.

Example 7

Process for Making High Strength Concrete with Novel CPSC Cement

This example shows that the phosphate modified Portland cement CPSC significantly improves the mechanical strength of concrete. The cements for testing are ordinary Type I Portland cement and phosphate-modified ordinary Type I Portland cement as described in Example 6. Coarse crushed rock (average size: 1.5 inch in diameter) and sand (average size: 0.01 inch) were used as aggregates. The compressive testing samples were prepared by mixing 22 wt % cement powder, 55 wt % coarse aggregates, 18% wt sand, and 5 wt % water. The concrete paste was cast into a mold of 10 cm×10 cm×10 cm by vibration packing method. The cast samples were incubated at 100% humidity at room temperature for 28 days before compressive testing. The samples were tested with an Instron Universal Testing Machine with a cross-head speed head of 2 mm/min. The average compressive strength of ordinary Portland cement concrete was 84 MPa, with the standard deviation of 6 MPa. The compressive strength of phosphate modified Portland cement CPSC concrete (where CPSC was prepared as described in Example 1) was 155 MPa, with the standard deviation of 10 MPa. It indicated that the CPSC cement composition of the present invention significantly improved the mechanical strength of the concrete.

It is to be recognized that various alterations, modifications, and/or additions may be introduced into the constructions and arrangements of parts described above without departing from the spirit or ambit of the present invention as defined by the appended claims.

What is claimed is:

1. A bio-active hydraulic cement composition for medical and dental applications that reacts with water at a substantially neutral PH, said hydraulic cement composition comprising:

at least one phosphate compound in an amount sufficient to react a major portion of calcium hydroxide produced during hydration of said cement to form hyroxyapatite or other calcium phosphates, said at least one phosphate compound being present in an amount within the range from more than 5% to about 30% by weight of said cement composition and being selected from the group consisting of:

calcium phosphates;
magnesium phosphates;
sodium phosphates;
zinc phosphates;
aluminum phosphates;
iron phosphates;
potassium phosphates;
nickel phosphates;
zirconium phosphates;
phosphloric acid, organo-metallic phosphates; and
mixtures thereof; and at least one calcium silicate compound said calcium silicate compound being selected from the group consisting of:
di-calcium silicate;
tri-calcium silicate;
tetra-calcium silicate; and
mixtures thereof.

2. The bio-active hydraulic cement composition of claim 1, wherein said phosphate compound is mono-calcium phosphate.

3. The bio-active hydraulic cement composition of claim 1, wherein said at least phosphate compound is selected from the group consisting of:
mono-phosphate ($PO_4^{-3}$) compounds;
di-phosphate ($P_2O_7^{-4}$) compounds;
tri-phosphate ($P_3O_{10}^{-5}$) compounds;
meta-phosphate compounds; and
mixtures thereof.

4. The bio-active hydraulic cement composition of claim 1, comprising said calcium silicate compound in an amount within the range from about 40% to about 80% by weight of said cement composition.

5. The bio-active hydraulic cement composition of claim 1, further comprising ancillary compounds which in total comprise less than about 30% by weight of said cement composition.

6. The bio-active hydraulic cement composition of claim 5, wherein said ancillary compounds are selected from a group consisting of:
silicon dioxide;
tricalcium aluminate;
tetra-calcium aluminoferrite;
calcium sulphate;
calcium sulphate dihydrate; and
mixtures thereof.

7. The bio-active hydraulic cement composition of claim 1, further comprising impurity compounds in an amount less than about 15% by weight of said cement composition.

8. The bio-active hydraulic cement composition of claim 4, when said impurity compounds are selected from a group consisting of:
iron oxides;
magnesium oxide;
potassium oxide;
sodium oxide;
sulphur oxides;
carbon dioxide;
water; and
mixtures thereof.

9. The bio-active hydraulic cement composition of claim 1, further comprising:
a radiopaque substance.

10. The bio-active hydraulic cement composition of claim 9, wherein said radiopaque substance is selected from a group consisting of:
gold;
silver;
barium;
bismuth;
tantalum;
barium sulphate;
bismuth oxide;
tantalum oxide;
zirconium oxide; and
mixtures thereof.

11. The bio-active hydraulic cement composition of claim 9, comprising said radiopaque substance in an amount within the range from about 3% to about 50% by weight of said cement composition.

12. The bio-active hydraulic cement composition of claim 11, comprising said radiopaque substance in an amount within the range from about 10% to about 30% by weight of said cement composition.

13. A high-strength hydraulic cement composition, comprising:
ordinary Portland cement; and
calcium phosphate in an amount sufficient to react a major portion of calcium
hydroxide produced during hydration of said cement to form hydroxyapatite or other calcium phosphates.

14. A high-strength hydraulic cement composition of claim 13, comprising said calcium phosphate in an amount in the range between about 10% and about 15% by weight of said cement composition.

15. The high-strength hydraulic cement of claim 14, wherein said calcium phosphate is selected from a group consisting of:
mono-calcium phosphate;
di-calcium phosphate; and
mixtures thereof.

16. The high-strength hydraulic cement of claim 14, wherein said calcium phosphate is mono-calcium phosphate.

* * * * *